United States Patent [19]

Attix

[11] Patent Number: 5,006,714
[45] Date of Patent: Apr. 9, 1991

[54] SCINTILLATOR DOSIMETRY PROBE
[75] Inventor: Frank H. Attix, Madison, Wis.
[73] Assignee: Radiation Measurements, Inc., Madison, Wis.
[21] Appl. No.: 315,321
[22] Filed: Feb. 24, 1989
[51] Int. Cl.$^5$ .............................................. G01T 1/29
[52] U.S. Cl. .............................. 250/368; 250/252.1; 250/336.1
[58] Field of Search .............. 250/368, 252.1 R, 336.1

[56] References Cited

U.S. PATENT DOCUMENTS

| | | | |
|---|---|---|---|
| 4,413,184 | 11/1983 | Marrone | 250/368 |
| 4,749,864 | 6/1988 | Sciamanda et al. | 250/368 X |
| 4,795,910 | 1/1989 | Henderson et al. | 250/368 X |
| 4,829,185 | 5/1989 | Cerff | 250/368 X |

FOREIGN PATENT DOCUMENTS

| | | | |
|---|---|---|---|
| 57-156575 | 9/1982 | Japan | 250/368 |
| 58-117477 | 7/1983 | Japan | 250/368 |

OTHER PUBLICATIONS

R. C. Lawson, et al., "(D,D) and (D,T) Neutron Depth Dose Measurements in a Tissue-Equivalent Phantom," *Phys. Med. Biol.*, vol. 12, No. 2, pp. 201–215.

"A Protocol for the Determination of Absorbed Dose from High-Energy Photon and Electron Beams", *Medical Physics*, vol. 10, No. 6, pp. 741–771, Nov./Dec., 1983.

L. D. Gager et al. "Silicon Diode Detectors Used in Radiological Physics Measurements, Part I: Development of an Energy Compensating Shield", *Medical Physics*, vol. 4, No. 6, Nov./Dec. 1977, pp. 494–502.

A. E. Wright et al. "Silicon Diode Detectors Used in Radiological Physics Measurements, Part II: Measurement of Dosimetry Data for High-Energy Photons", *Medical Physics*, vol. 4, No. 6, Nov./Dec. 1977, pp. 499–502.

A. S. Beddar et al., "TE Scintillation Detector for High-Energy Photon and Electron Beam Dosimetry" abstract of oral presentation before World Congress on Medical Physics & Biomedical Eng., San Antonio, Tex., presented 8/6–12/88.

A. S. Beddar et al., "Ionizing Radiation Effects on Optical Fibers" abstract of oral presentation before the World Congress on Medical Physics and Biomedical Engineering, San Antonio, Tex., presented Aug. 6–12, 1988.

*Primary Examiner*—Constantine Hannaher
*Assistant Examiner*—Jacob M. Eisenberg
*Attorney, Agent, or Firm*—Quarles & Brady

[57] ABSTRACT

A probe (10) employs a scintillator (18) as a detector for high-energy beam dosimetry. The scintillator (18) is positioned in an ionizing radiation beam (52) which creates a light output that is proportional to the radiation dose-rate incident upon the scintillator (18). The light is conducted from the scintillator (18) through a light pipe (16) to a photomultiplier tube (28), which converts the light to an electric current. The scintillator (18), the light pipe (16), the photomultiplier (28), and associated optical connections have opaque coverings or sheaths to prevent extraneous light from being introduced into the probe (10). The electric current produced by the photomultiplier tube (28) is proportional to the radiation dose-rate incident upon the scintillator (18). The radiation dose-rate may then be displayed or recorded by a measurement of the electric current. The light pipe (16) is flexible so that the scintillator (18) may be repositioned in a number of locations in the radiation beam (52) to map the radiation field. The scintillator (18) is made of a material that approximates water or muscle tissue in atomic number and electron density to minimize perturbations in a phantom water tank (50). A compensating light pipe 60, paralleling the first, and connected to a second photomultiplier tube, generates a current that, when subtracted from the first photomultiplier tube current, corrects for radiation interactions in the light pipe and photomultiplier tube.

8 Claims, 3 Drawing Sheets

SCINTILLATOR DOSIMETRY PROBE

FIELD OF THE INVENTION

This invention relates to devices used to analyze the spatial distribution of radiation therapy application equipment.

BACKGROUND OF THE INVENTION

A common therapy for cancerous tumors is radiation treatment, usually by x-rays, gamma rays, or fast electrons, or sometimes by neutrons or heavy charged particles. The success of radiation treatment depends upon the ability of a therapy team to heavily irradiate the tumor volume while delivering a comparatively minimal amount of absorbed dose, or energy imparted per unit mass, to healthy body tissue. To characterize the spatial distribution of dose in a beam of radiation, before applying the radiation dose to the human body, it is common practice to measure the dosage of an impinging radiation beam at a large number of locations throughout a cube-shaped water tank called a "phantom." This is referred to as "mapping the radiation field."

The usual detector employed for taking measurements of the radiation field is a cavity-type ionization chamber attached to a computer-controlled scanning mechanism that is programmed to move throughout the volume of interest. At each point sequentially occupied by the cavity ion chamber, the desired physical quantity to be measured is the absorbed dose in the undisturbed water, i.e., the dose that would be absorbed in the absence of the cavity ion chamber, since the cavity ion chamber perturbs the radiation field. The procedure for interpretation of the electric charge collected in the cavity ion chamber to derive the value of the absorbed dose in water is very complex and error-prone, as described in such documents as "A Protocol for the Determination of Absorbed Dose from High-Energy Photon and Electron Beams," *Medical Physics,* vol. 10, no. 6, pp. 741-771, November/December 1983. A major disadvantage of the cavity ion chamber is its size (typically 0.1-1.0 cubic centimeters, 1-2 cm in length), which limits the spatial resolution obtainable with such a detector. Smaller cavity ion chambers would suffer from inadequate sensitivity.

Another detector that is sometimes used for mapping the radiation field in the phantom, in place of a cavity ion chamber, is the silicon diode. The silicon diode has the advantages of being smaller than a cavity ion chamber and of being made of a solid instead of a gas, thus avoiding the so-called "displacement or void correction" that must be applied to the cavity ion chamber to account for the lack of beam attenuation in the volume of water displaced by the gas (usually air) in the ion chamber. The offsetting disadvantages of silicon diodes are that they have an atomic number of 14, as compared to one for the hydrogen and 8 for the oxygen in the surrounding water, and their density is 2.3 times that of water. The higher atomic number causes excessive response of the dosimeter to low-energy scattered photons in x-ray or gamma ray beams, and excessive scatter in electron beams. The higher density also perturbs the electrons in the vicinity, thus affecting the dosimeter reading. An example of the use of a silicon diode as a radiation field-mapping probe was published by L. D. Gager et al., "Silicon Diode Detectors Used in Radiological Physics Measurements. Part I: Development of an Energy Compensating Shield," *Medical Physics,* vol. 4, no. 6, p. 494-498, November/December 1977, and by A. E. Wright et al., "Silicon Diode Detectors Used in Radiological Physics Measurements. Part II: Measurement of Dosimetry Data for High-Energy Photons," *Medical Physics,* vol. 4, no. 6, pp. 499-502, November/December 1977.

SUMMARY OF THE INVENTION

In accordance with the present invention, a scintillator is applied as a detector for high-energy beam dosimetry. The invention principally comprises a scintillator, a flexible light pipe, and a photomultiplier tube which converts light to electric current or charge. A first end of the light pipe is optically connected to the scintillator and forms a free end that may be moved. A second end of the light pipe is fixedly and optically connected to the photomultiplier tube. The scintillator is positioned within an ionizing radiation beam where the radiation incident upon the scintillator creates a flash of light from the ionization of a phosphor in the scintillator. The light is conveyed to the light pipe and then to the photomultiplier tube, which converts the light to an electric current that is directly proportional to the absorbed dose-rate in the scintillator.

The invention may be used as a dosimetry probe to map the radiation field in a water tank, or phantom, to characterize the spatial distribution of dose in a beam of radiation before applying the radiation dose to a human body. The free end of the scintillator dosimetry probe of the present invention is readily moved to take dose-rate measurements at a number of locations within the phantom. The scintillator and an enclosure about the scintillator are composed of a solid material that approximates the atomic number and electron density of water (or muscle tissue). The use of a solid material in the scintillator and the scintillator enclosure eliminates the need for a displacement or void correction that is necessary in the use of cavity ion chambers as detectors for high-energy beam dosimetry. The use of a material that is of comparable atomic number and electron density to that of water (or muscle tissue) eliminates the problems of excessive dosimeter response to low-energy scattered photons in x-ray or gamma ray beams and excessive scatter in electron beams that are inherent in the use of silicon diodes as detectors.

Further objects, features, and advantages of the invention will be apparent from the following detailed description taken in conjunction with the accompanying drawings.

DESCRIPTION OF THE PREFERRED EMBODIMENT

Figure 1:
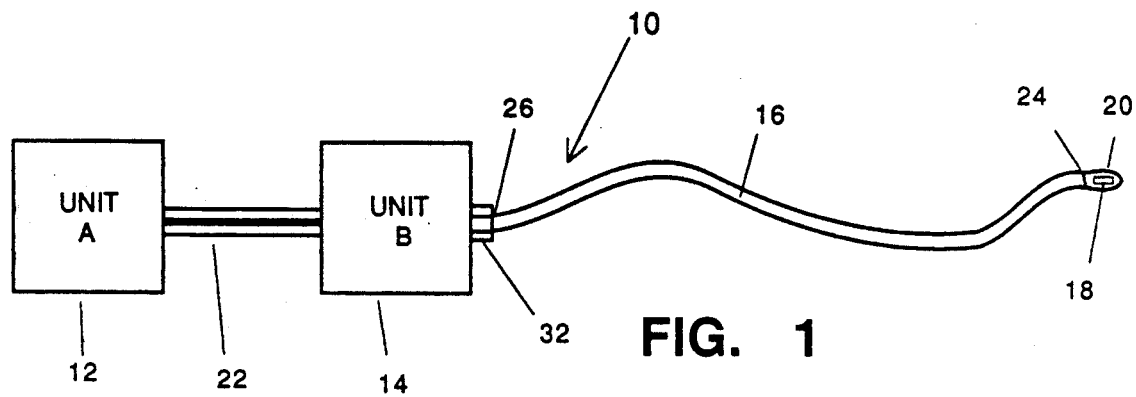
FIG. 1 is a schematic diagram of a scintillator dosimetry probe constructed in accordance with the present invention.

With reference to the drawings, a scintillator dosimetry probe in accordance with the present invention is shown at 10 in FIG. 1. The scintillator dosimetry probe 10 comprises a base unit 12, an optical-to-electrical conversion unit 14, a flexible small-diameter light pipe 16, a scintillator 18, and a scintillator enclosure 20. The base unit 12 and the optical-to-electrical conversion unit 14 are connected by a triaxial cable 22, or by two coaxial cables. The base unit 12 and the optical-to electrical conversion unit 14 are shown as separate, though they may be contained in a single box. The light pipe 16 has a first end 24 and a second end 26. The first end 24 of the light pipe 16 is optically connected to the scintillator 18 and is a free end that may be moved. The second end 26 of the light pipe 16 is fixedly and optically connected to the optical-to-electrical conversion unit 14, which is stationary.

Figure 2:
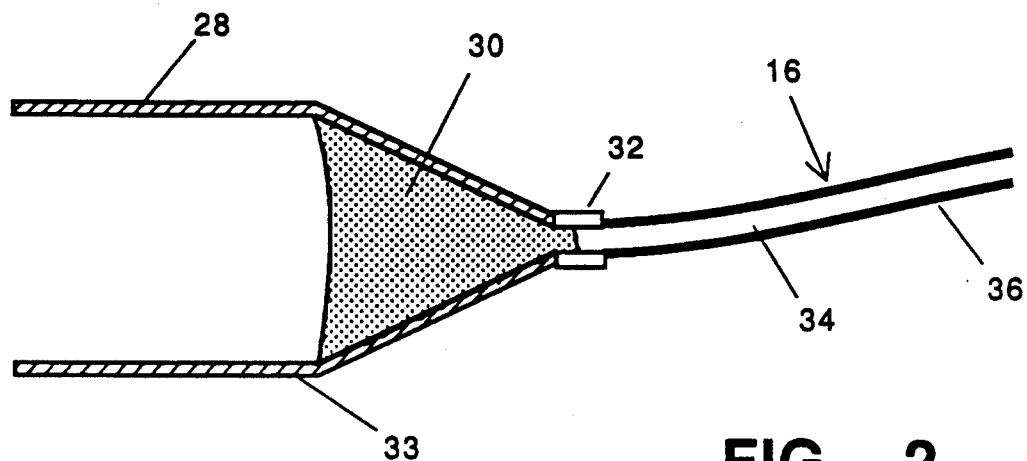
FIG. 2 is a schematic cross-section diagram of a typical connection of the light pipe to a photomultiplier tube.

The base unit 12 contains a high voltage power supply and such additional amplifiers and controls as are necessary. The base unit 12 also includes suitable displays and/or recording devices to display an output indicative of ionizing radiation detected by the scintillator 18. The display may be either digital or analog, and the recordation may be in a computer memory or a hard copy. The optical-to-electrical conversion unit 14 converts light indicative of ionizing radiation detected by the scintillator 18 to an output signal in the form of an electric current or charge. The optical-to-electrical conversion unit 14 includes in its interior a photomultiplier tube 28 and associated voltage divider, an optical coupler 30, and an optical connector 32. The photomultiplier tube 28, the optical coupler 30, and the optical connector 32 are shown as a schematic cross-section in FIG. 2. It is to be understood that other devices for converting light energy to an electrical signal may be used in place of the photomultiplier 28. The photomultiplier tube 28 is butted against the optical coupler 30 which joins through the optical connector 32 to the light pipe 16. The optical coupler 30 and the optical connector 32 have an optical coupling cement or grease distributed at contact points to maximize the light transfer from the light pipe 16 to the photomultiplier tube 28. The photomultiplier tube 28 and the optical coupler 30 have an opaque enclosure 33 which serves to keep the optical-to-electrical conversion unit 14 light-tight with respect to the photomultiplier tube 28, except for the opening to the light pipe 16. The optical coupler 30 as shown may preferably be composed of Lucite for its light-conductive characteristics, but other suitable light-conducting materials and configurations may be substituted within the present teaching.

Figure 5:
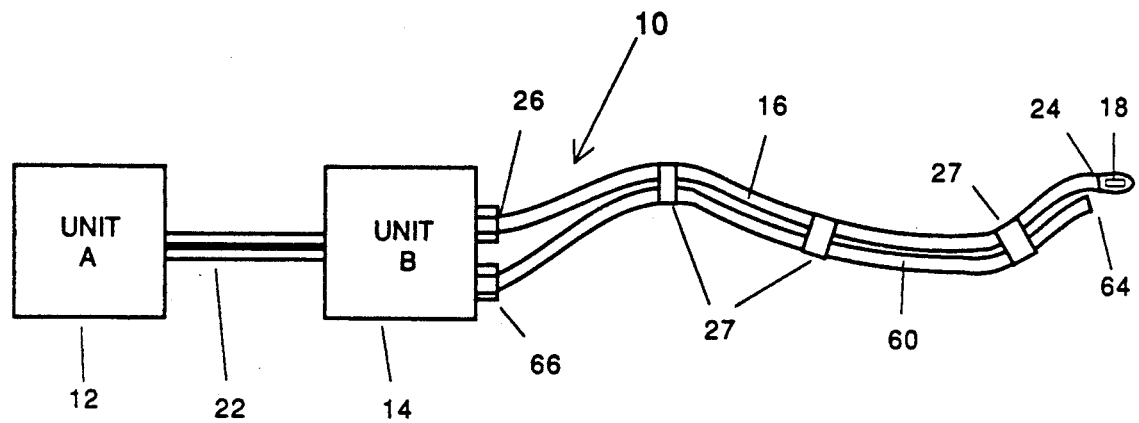
FIG. 5 is a schematic diagram of an alternative embodiment of a scintillator dosimetry probe incorporating a compensating light pipe used to compensate for stray light generation.

The light pipe 16 is comprised of a single fiber or a bundle of fibers 34 enclosed in an opaque sheath or sheaths 36, according to usual fiber-optic design practice. The light pipe 16 serves to conduct light from the scintillator enclosure 20 to the photomultiplier tube 28. The material of the fiber 34 must be resistant to radiation discoloration damage. The material of the fiber 34 should produce a negligible level of stray light generation when it is struck by radiation. Otherwise a second, parallel compensating light pipe 60, connected to a second photomultiplier tube but not to a scintillator, may be required to compensate for this stray light signal. The implementation of a compensating light pipe 60 is shown in FIG. 5. The compensating light pipe 60 is analogous to the first light pipe 16, having a first end 64 and a second end 66. The light pipes are run parallel to one another and are attached by tape 27, contained within a common plastic tube, or otherwise fastened together. As shown in FIG. 5, the compensating light pipe 60 leads into the optical-to-electrical coupling unit 14 independently, where it enters a photomultiplier tube by a configuration similar to that of FIG. 2. The signal created by stray light generated in the compensating light pipe 60 can be subtracted from the signal created by the light pipe 16 so as to compensate for the stray light detected by the light pipe 16. The subtraction of the stray light signal is accomplished within the optical coupling unit 14 instrumentally, for example, by inverting the stray light signal and adding it to the signal of the light pipe 16. Fused silica is a preferable fiber material of both the light pipes 16 and 60 because of its well-known resistance to radiation damage. Flexibility of the light pipes 16 and 60 is required to allow the scintillator 18 to be moved about to map the dose-rates in a radiation field, as explained further below.

The material of the scintillator 18 is chosen to be as much like water (or human muscle tissue) as possible with respect to atomic number and electron density (electrons/cm$^3$). A suitable material for the scintillator 18 is polyvinyltoluene, consisting essentially of hydrogen and carbon, which has a specific gravity of 1.032, and an electron density of $3.37 \times 10^{23}$ electrons per gram. Water, comparatively, has an electron density of $3.34 \times 10^{23}$ electrons, a 1% difference. Other suitable commercially available materials include Bicron 400 or 408, and anthracene. The scintillator 18 is made small enough to give good spatial resolution in dose-rate measurements. For example, for x-rays or gamma rays a right circular cylinder that is approximately 2 mm in diameter by 2-3 mm in length is acceptable, assuming that the light output will be great enough at typical radiotherapy x-ray dose-rates of 0.1-1 Gy/min (1 Gy=1 gray=1 joule/kg). The scintillator 18 may be made smaller when used with electron beams, which have higher dose-rates than x-ray beams and typically show steeper spatial variations. For use with electron beams, the scintillator 18 may be sized at approximately a 1 mm diameter by a 2 mm length. It is to be noted that as the volume of the scintillator 18 is decreased, background light competition from the irradiated part of the fiber-optic light pipe 16 becomes more significant, which is one limitation on how small the scintillator 18 can be, unless a compensating light pipe 60 is employed. Another limitation is the efficiency of the optical coupler 30 and the optical connection 32, i.e., the fraction of light that reaches the photomultiplier tube 28. The lower the efficiency of the coupler 30 and the connection 32, the larger the scintillator 18 that is required. The current of the photomultiplier tube 28 when dark must also be negligible when compared to the signal current.

Figure 3A:
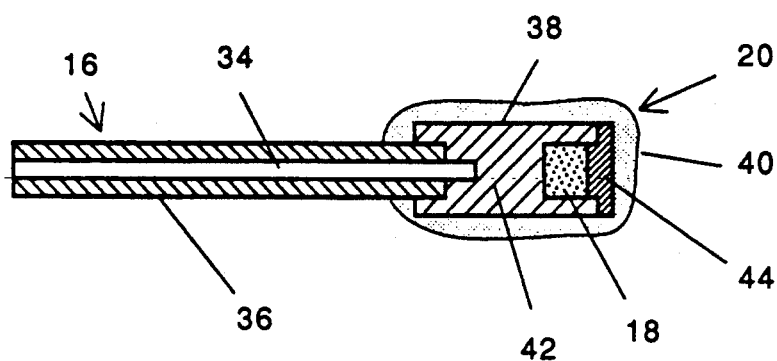
FIG. 3A is a typical scintillator mounting adapted for use with irradiation by an x-ray beam.
Figure 3B:
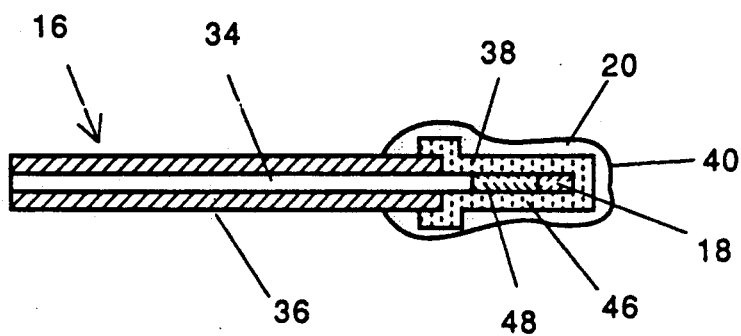
FIG. 3B is a typical scintillator mounting adapted for use with irradiation by an electron beam.

FIGS. 3A and 3B show typical mountings of the scintillator 18 within the scintillator enclosure 20 as adapted for use for irradiation by x-ray and electron beams, respectively. The scintillator enclosure 20 comprises a light conducting assembly 38 which encloses the scintillator 18, and opaque coating 40 which envelops the light conducting assembly 38. The scintillator enclosure 20 must be enveloped on all sides by the opaque coating 40 except where the scintillator enclosure 20 connects with the light pipe 16. The opaque coating 40 is typically a thin, waterproof plastic dip. The scintillator enclosure 20 should simulate water just as the scintillator 18 does, to avoid perturbing the radiation field. Where the optic fiber or fibers 34 are chosen to be dissimilar from water (e.g., silica) in order to avoid radiation damage to, or light generation in the fibers, then a short section of plastic (e.g. polystyrene) light pipe or light conductor is optically coupled between the scintillator 18 and the optic fiber or fibers 34 to avoid the perturbation of electrons that result from the proximity of the higher atomic number silica ($SiO_2$) to the scintillator 18.

FIGS. 3A and 3B show different mounting arrangements of the scintillator 18 within the scintillator enclosure 20. For the embodiment of FIG. 3A, the scintillator 18 is enveloped by the light conducting assembly 38 which comprises a light conducting holder 42 and a light conducting plug 44; for the case of FIG. 3B, the scintillator 18 is enveloped by an alternate arrangement of a light conducting holder 46 and a light conducting coupler 48. The light conducting assembly 38 and associated parts—holder 42, plug 44, holder 46, and coupler 48—are preferably composed of polystyrene plastic because of its light-conductive characteristics and because of its approximation of water in atomic number and density. Optical coupling cement is used to connect the optic fiber or fibers 34 and the scintillator 18 with the holders, couplers, and plugs. Many other configurations are possible for the mounting of the scintillator 18, so long as the water (or tissue) equivalence is maintained, along with adequate optical coupling and exclusion of external light and moisture. The use of a reflecting coating on the outside of the light conducting assembly 38 to improve optical coupling should be avoided if it compromises the water-equivalence. Examples of such reflecting coatings include MgO and aluminum, both of which are too high in atomic number to be tolerable so near the scintillator 18 unless the coatings are very thin.

Figure 7:
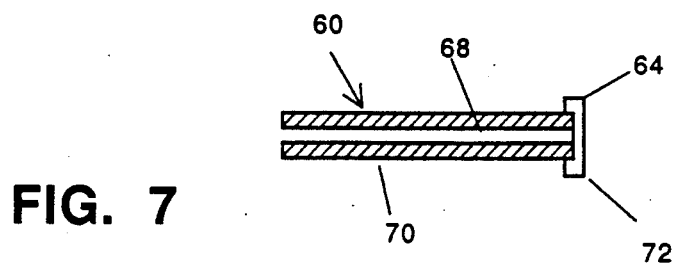
FIG. 7 is a typical end of a compensating light pipe that is to be irradiated by an x-ray beam.

FIG. 7 shows a preferably configuration of the first end 64 of the second, compensating light pipe 60. The compensating light pipe 60 has an optic fiber or fibers 68 identical in number and material to the fiber or fibers 34 of the first light pipe 16. The optic fiber or fibers 68 is contained in an independent sheath or sheaths 70. The end is capped with opaque plastic dip 72.

Figure 4:
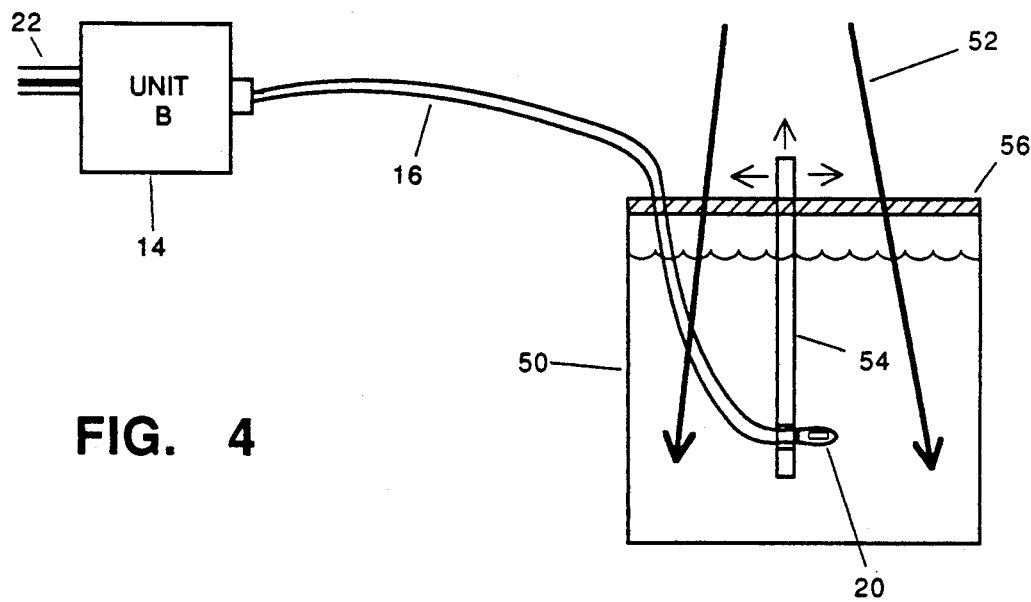
FIG. 4 is a schematic diagram showing the insertion of the scintillator dosimetry probe into a water-filled phantom.

The scintillator dosimetry probe 10 is used to study x-ray, gamma ray, and electron beams in preparation for radiotherapy cancer treatment. As shown in FIG. 4, the free end of the scintillator dosimetry probe 10 (the first end 24 of the light pipe 16 to which the scintillator 18 is optically connected) is submerged in a water-filled plastic-walled cube 50, the cube 50 commonly referred to as a "phantom." A radiation beam 52 (x-ray, gamma ray or electron beam) impinges upon the cube 50 and the scintillator 18 gauges the radiation dose-rate at the point at which the scintillator 18 is positioned within the cube 50. A computer-driven mechanical 2- or 3-dimensional scanner 54 and associated scanner drive 56 is used to reposition the free end of the probe 10 (the first end 24 of the light pipe 16 to which the scintillator 18 is optically connected) at a number of points within the cube 50 to form a map of the radiation field to which the cube 50 is exposed. The scanner 54 is attached near the first end 24 of the light pipe 16. The light pipe 16 is flexible and has enough slack so that the scintillator 18 may be moved throughout the cube 50 while allowing the optical-to-electrical conversion unit 14 to remain stationary outside of the radiation field. If the optical-to-electrical conversion unit 14 is to be placed inside the room containing the radiation beam 52, the photomultiplier tube 28 must be shielded from scattered x-rays. However, to the extent that the second photomultiplier tube that serves the compensating light pipe is similarly irradiated by scattered x-rays, the resulting electric current will be cancelled. Preferably, the optical-to-electrical conversion unit 14 is located outside that room, so such shielding or compensation will not be required. The scintillator dosimetry probe 10 is substitutable for other detectors commonly used to map the radiation field to which the cube 50 may be exposed, e.g. cavity ion chambers or silicon diodes. The use of the scintillator dosimetry probe 10 in body openings or against the skin of live patients is also foreseen, as well as applications in health physics (radiation protection) especially in "hostile" locations where harsh environmental conditions may cause malfunction of cavity ion chamber detectors.

Figure 6:
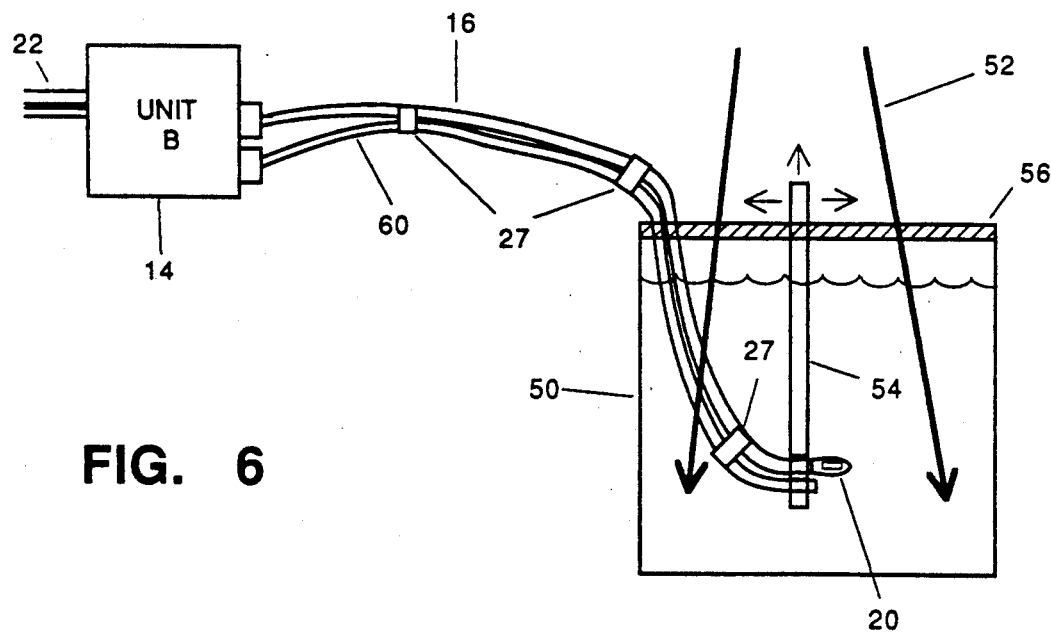
FIG. 6 is a schematic diagram showing the insertion of the scintillator dosimetry probe incorporating the compensating light pipe into a water-filled phantom.

FIG. 6 shows the implementation of the present invention with the scanner 54 and the second, compensating light pipe 60. As shown in FIG. 6, in this embodiment the end of the compensating light pipe 60 moves in close conjunction to the scintillator enclosure 20 at the end of the light pipe 16 so that the compensation for stray light can be continuously accomplished as the scanner 54 moves the scintillator probe through the cube 50.

In the operation of the scintillator dosimetry probe 10, the exposure of the scintillator 18 to incident radiation from the radiation beam 52 creates a flash, or multitude of flashes, of light from the ionization of a phosphor. The light is conducted from the scintillator 18 through the light conducting assembly 38 and on through the optic fiber or fibers 34. The light is further carried through the optical connection 32 and the optical coupler 30, where it enters the photomultiplier tube 28. The photomultiplier 28 converts the incident light to an electric current, or charge, that is directly proportional to the absorbed dose-rate, or the absorbed dose, respectively, in the scintillator 18. The electric current or charge is carried via the cable or cables 22 to the base unit 12. The base unit 12 contains a voltage amplifier for current or charge and a display or recordation of the current or charge reading. The base unit 12 also generates a high voltage supply that is carried to the second unit 14 via the cable or cables 22 which supplies the necessary power for the photomultiplier tube or tubes 28.

In this way, a dosimetry probe is described which is accurate and flexible for creating two or three dimensional profiles of therapeutic radiation closing devices. Since the dosimetry probe enables quick, accurate and relatively fine-scale positional analysis of the energy field produced by a radiation therapy instrument. Since the base unit 12 and optical-to-electrical conversion unit 14 are connected to the scintillator by the light pipe 16, they may actually be located some distance from the radiation therapy site, perhaps in an adjacent room, so that it may be easily shielded from the radiation source.

It is understood that the invention is not confined to the particular construction and arrangement of parts herein illustrated and described, but embraces such modified forms thereof as come within the scope of the following claims.

What is claimed is:

1. Apparatus for characterizing a radiation field by measuring the dose-rate at a plurality of points in the radiation field, the apparatus comprising:
   a phantom filled with water in the radiation field;
   a scintillator positioned in the phantom, the scintillator producing a light output proportional to the dose-rate of radiation that impinges upon the scintillator;
   a light pipe having a first end and a second end, the first end being optically connected to the scintillator so that the light pipe conveys the light output from the scintillator;
   means connected to the second end of the light pipe and located outside of the phantom for converting light to an output signal proportional to the dose-rate of radiation that impinges upon the scintillator; and
   mechanical scanning means for moving the scintillator with the end of the light pipe attached through the interior of the phantom to map the radiation field within the phantom.

2. An apparatus as claimed in claim 1 further comprising a waterproof scintillator enclosure that envelopes the scintillator and optically connects it to the light pipe.

3. An apparatus as claimed in claim 1 wherein the material of the scintillator is selected to have an electron density within about 1% of the electron density of water, $3.34 \times 10^{23}$ electrons per gram.

4. An apparatus as claimed in claim 3 wherein the material of the scintillator is polyvinyltoluene.

5. Apparatus for characterizing a radiation field by measuring the dose-rate at a plurality of points in the radiation field, the apparatus comprising:
   a phantom filled with water in the radiation field;
   a scintillator positioned in the phantom, the scintillator producing a light output proportional to the dose-rate of radiation that impinges upon the scintillator;
   a first light pipe having a first end and a second end, the first end being optically connected to the scintillator so that the first light pipe conveys the light output from the scintillator;
   a second light pipe having a first end and a second end, the first end being positioned adjacent the first end of the first light pipe to convey stray light in the phantom through the second light pipe;
   separate means connected to the second end of each of the first and second light pipes and located outside of the phantom for converting light to an output signal proportional to the dose-rate of radiation that impinges upon the scintillator and the first end of the second light pipe respectively;
   means for subtracting the output signal representing the stray light from the output signal representing the dose-rate of radiation that impinges upon the scintillator; and
   mechanical scanning means for moving the scintillator with the end of the light pipe attached through the interior of the phantom to map the radiation field within the phantom.

6. An apparatus as claimed in claim 5 further comprising a waterproof scintillator enclosure that envelopes the scintillator and optically connects it to the light pipe.

7. An apparatus as claimed in claim 6 wherein the material of the scintillator is selected to have an electron density within about 1% of the electron density of water, $3.34 \times 10^{23}$ electrons per gram.

8. An apparatus as claimed in claim 7 wherein the material of the scintillator is polyvinyltoluene.

* * * * *